United States Patent
Kurosawa et al.

(10) Patent No.: US 9,541,602 B2
(45) Date of Patent: Jan. 10, 2017

(54) ELECTRONIC COMPONENT INSPECTION APPARATUS AND METHOD

(71) Applicant: FUJITSU LIMITED, Kawasaki-shi, Kanagawa (JP)

(72) Inventors: Hiroshi Kurosawa, Kawasaki (JP); Masayuki Itoh, Kawasaki (JP); Kiyokazu Moriizumi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 252 days.

(21) Appl. No.: 14/466,500

(22) Filed: Aug. 22, 2014

(65) Prior Publication Data

US 2014/0361782 A1 Dec. 11, 2014

Related U.S. Application Data

(63) Continuation of application No. PCT/JP2012/056028, filed on Mar. 8, 2012.

(51) Int. Cl.
*G01R 31/311* (2006.01)
*G01N 21/956* (2006.01)
(Continued)

(52) U.S. Cl.
CPC .......... *G01R 31/311* (2013.01); *G01N 21/956* (2013.01); *G01N 21/95684* (2013.01);
(Continued)

(58) Field of Classification Search
CPC ................ G01R 31/311; G01N 21/956; G01N 2021/95638
See application file for complete search history.

(56) References Cited

U.S. PATENT DOCUMENTS 5,598,345 A * 1/1997 Tokura ................... G01N 21/88
382/145
2005/0270524 A1* 12/2005 Wang ................... G01N 21/956
356/326
(Continued)

FOREIGN PATENT DOCUMENTS

JP 03-199947 A 8/1991
JP 03-215704 A 9/1991
(Continued)

OTHER PUBLICATIONS

JPOA—Office Action mailed on Aug. 25, 2015 issued with respect to the corresponding Japanese Patent Application No. 2014-503385, with partial English translated office action.
(Continued)

*Primary Examiner* — Christopher Mahoney
(74) *Attorney, Agent, or Firm* — Fujitsu Patent Center

(57) ABSTRACT

An electronic component inspection apparatus includes a light source arranged in a mounting area where at least one electronic component is mounted to a board and a light-receiving sensor arranged outside the mounting area to detect an intensity of a light received from the light source. A computer executes a program to perform a process of determining a state of joining parts in the mounting area based on a result of comparison of the intensity of the light received by the light-receiving sensor with an intensity of distribution previously acquired.

9 Claims, 16 Drawing Sheets

(51) Int. Cl.
*H05K 1/02* (2006.01)
*G01R 31/02* (2006.01)
*H05K 3/34* (2006.01)

(52) U.S. Cl.
CPC ......... *G01R 31/026* (2013.01); *H05K 1/0269* (2013.01); *G01N 2021/95638* (2013.01); *H01L 2224/16225* (2013.01); *H05K 3/3436* (2013.01); *H05K 2201/10106* (2013.01); *H05K 2201/10734* (2013.01)

(56) References Cited

U.S. PATENT DOCUMENTS

| | | | | |
|---|---|---|---|---|
| 2005/0271258 | A1* | 12/2005 | Rowe | G06K 9/00046 382/124 |
| 2008/0141795 | A1* | 6/2008 | Gagnon | G01N 21/95684 73/865.8 |
| 2010/0035228 | A1* | 2/2010 | Jackson | B01D 57/02 435/5 |
| 2010/0124370 | A1 | 5/2010 | Saito et al. | |
| 2012/0127463 | A1* | 5/2012 | Hong | G01N 21/8806 356/237.5 |
| 2012/0154798 | A1* | 6/2012 | Suzuki | G01N 21/956 356/237.5 |
| 2012/0327215 | A1* | 12/2012 | Case | G01N 21/8806 348/92 |

FOREIGN PATENT DOCUMENTS

| | | |
|---|---|---|
| JP | 05-267420 A | 10/1993 |
| JP | 10-122828 A | 5/1998 |
| JP | 11-190703 A | 7/1999 |
| JP | 2000-346622 A | 12/2000 |
| JP | 2001-094249 A | 4/2001 |
| JP | 2001-144147 A | 5/2001 |
| JP | 2002-116011 A | 4/2002 |
| JP | 2006-041167 A | 2/2006 |
| JP | 2009-170699 A | 7/2009 |
| JP | 2010-123182 A | 6/2010 |
| JP | 2011-122820 A | 6/2011 |

OTHER PUBLICATIONS

International Search Report, mailed in connection with PCT/JP2012/056028 and mailed Apr. 10, 2012 (Total number of pp. 2).

* cited by examiner

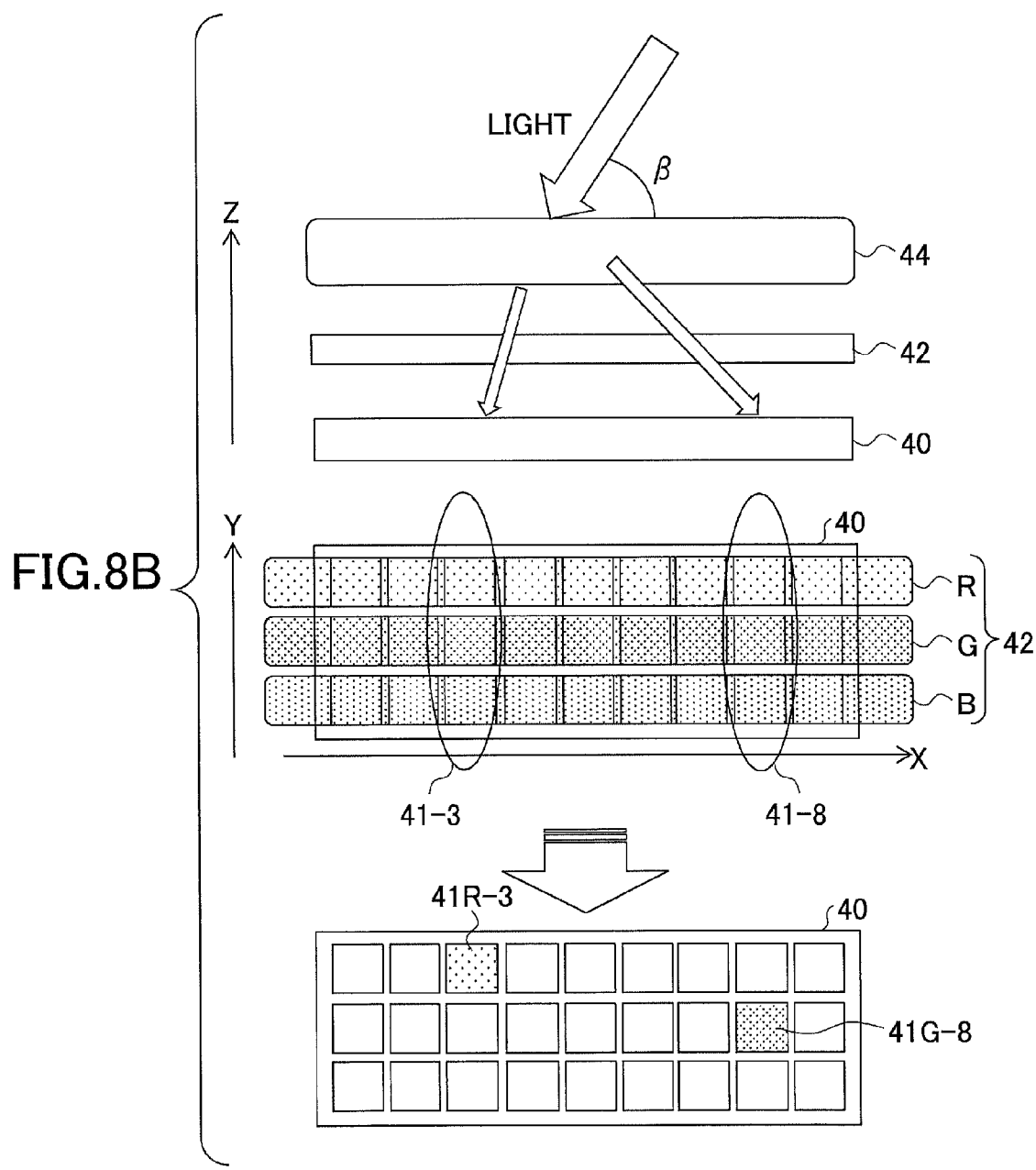

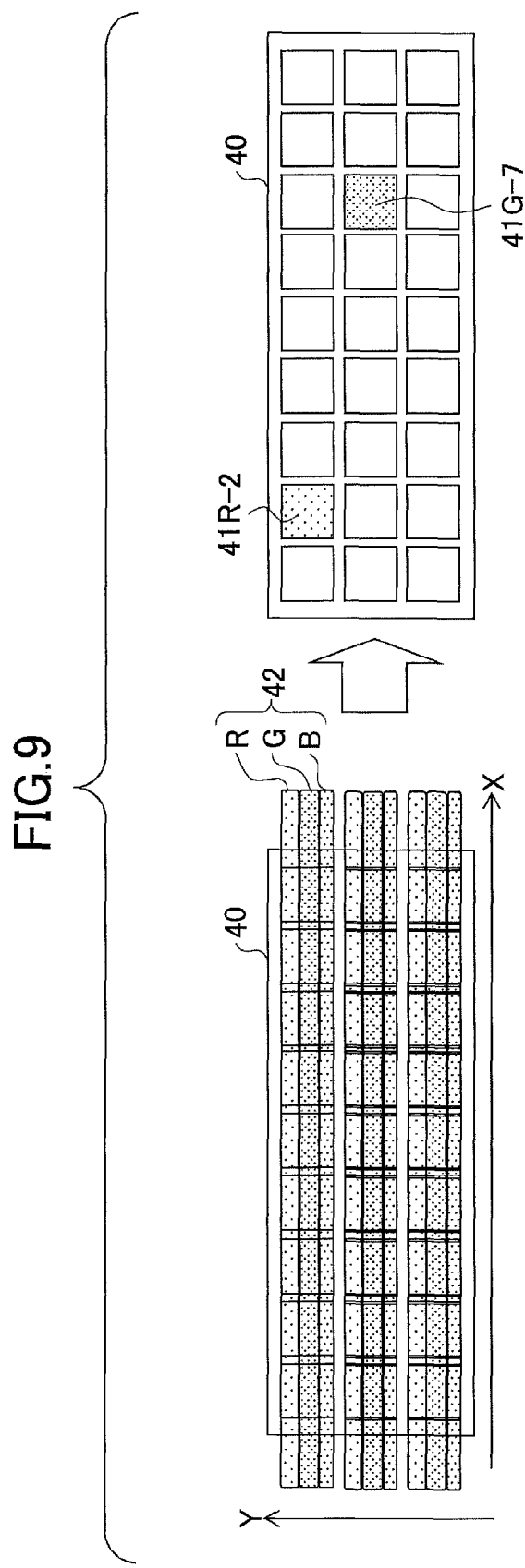

FIG.10
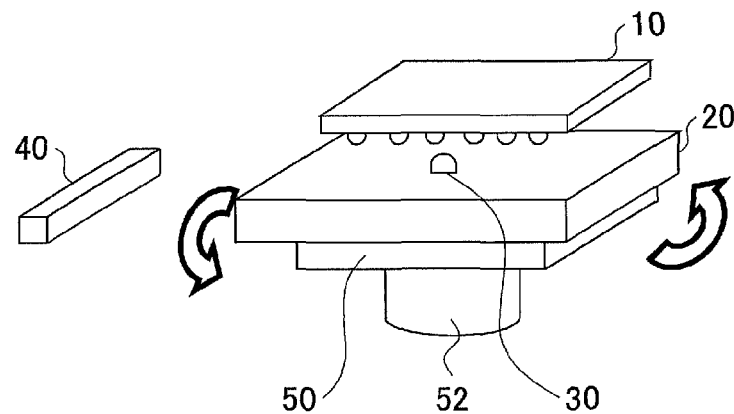
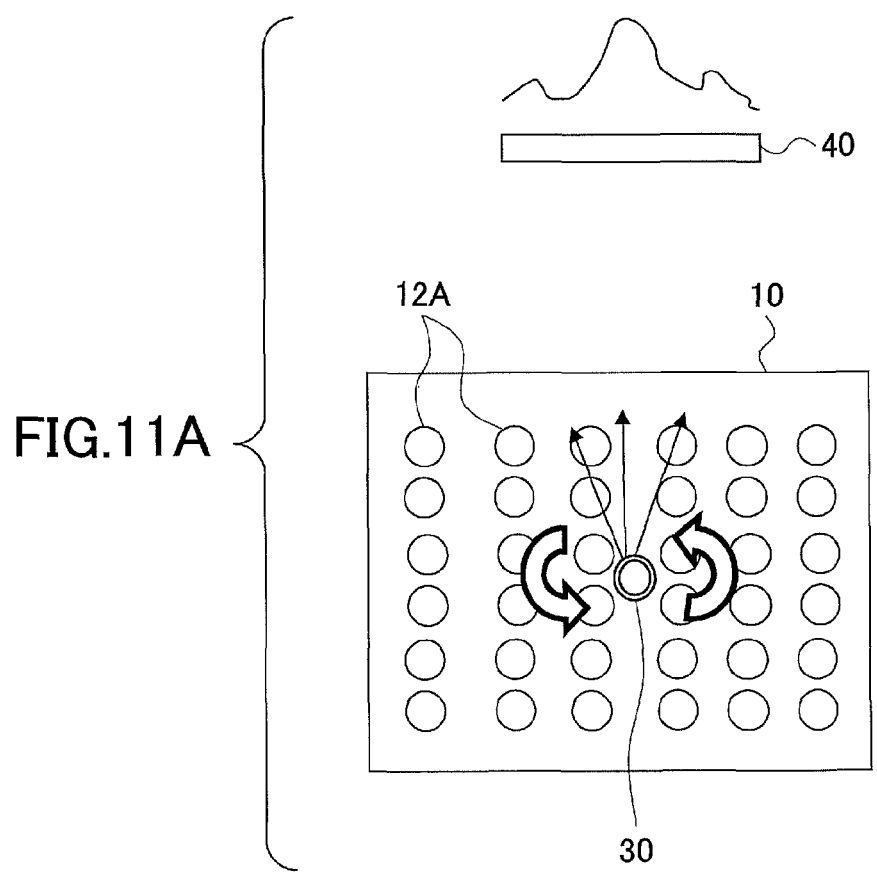
FIG.11A

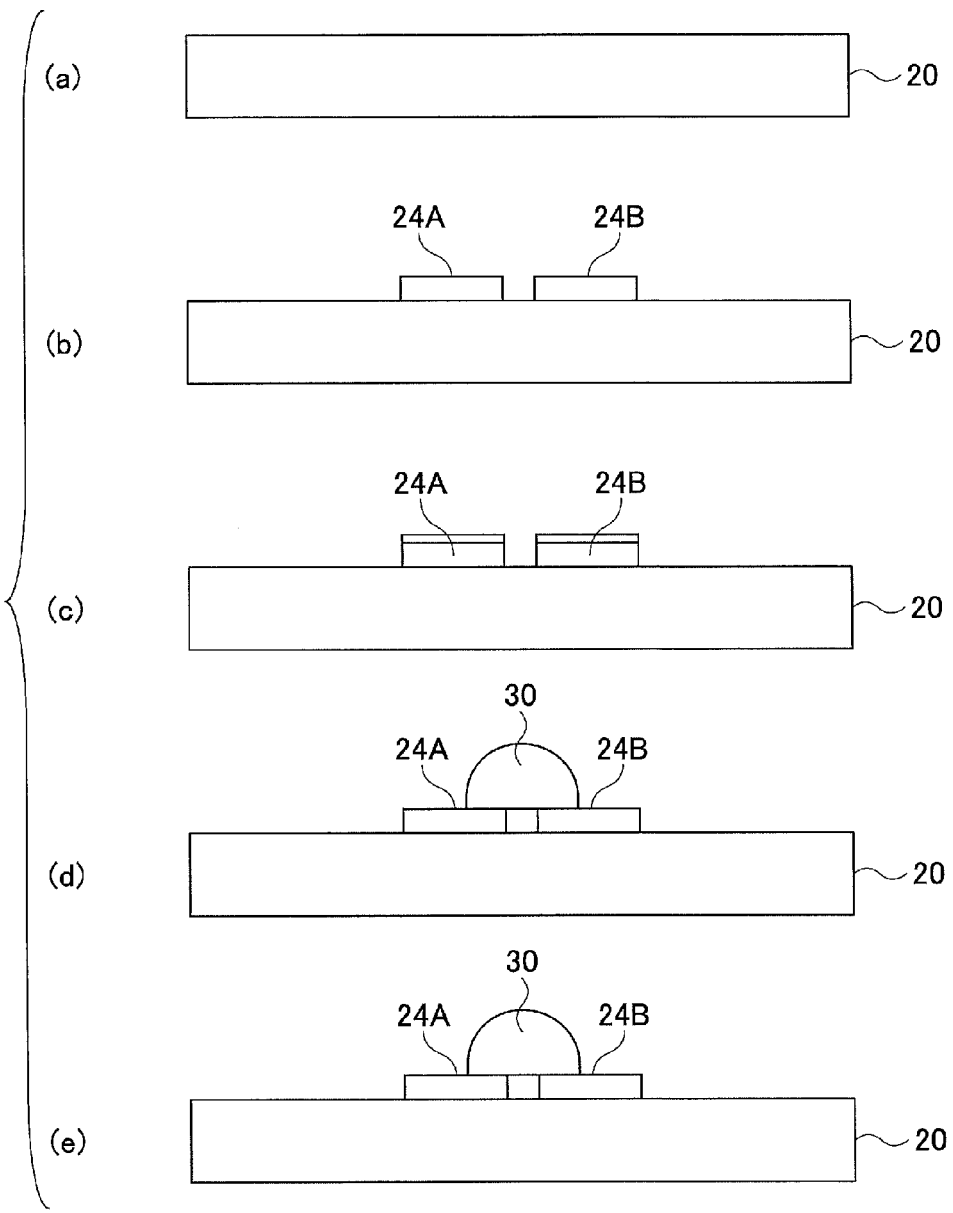

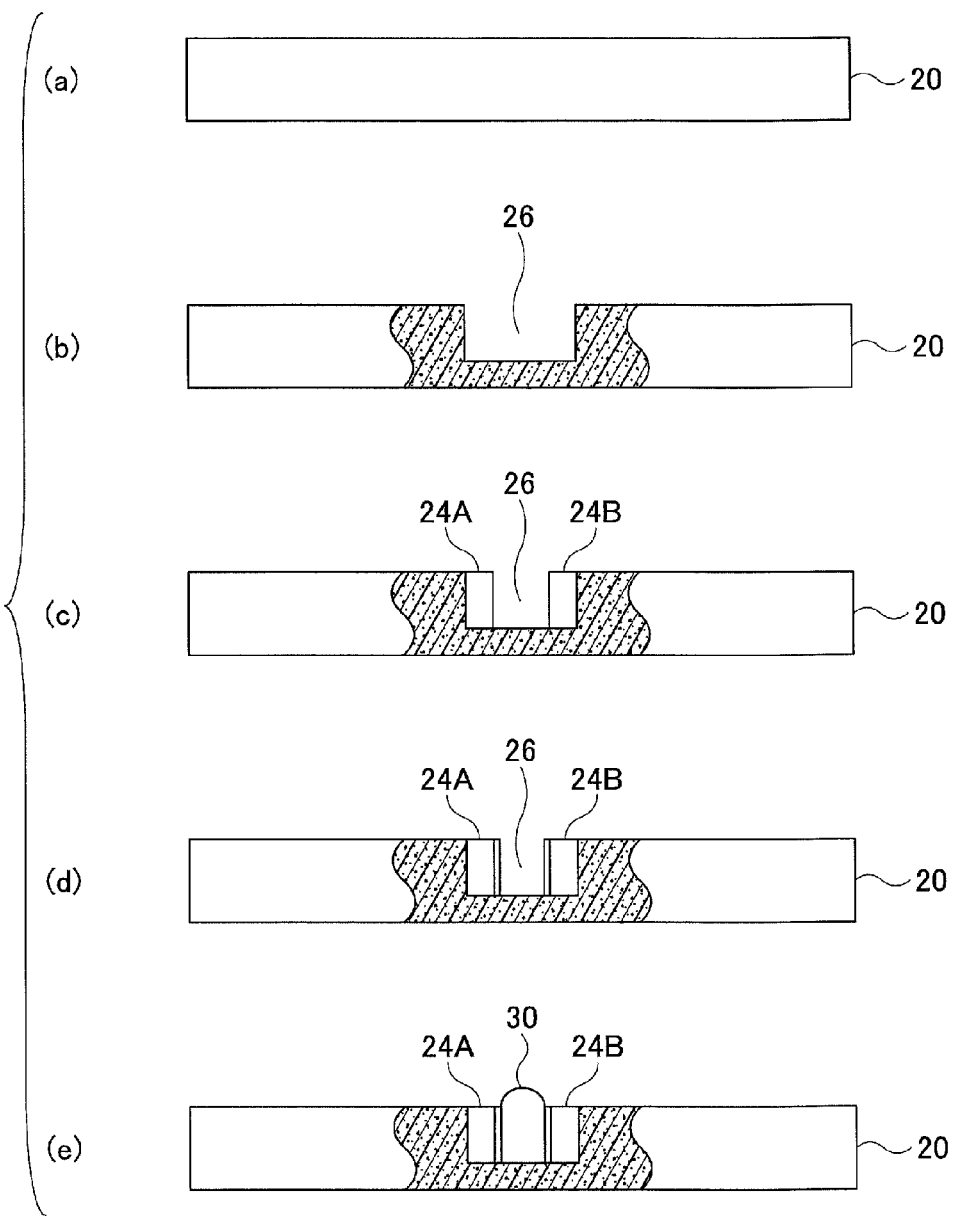

ELECTRONIC COMPONENT INSPECTION APPARATUS AND METHOD

CROSS-REFERENCE TO RELATED APPLICATIONS

The present application is a continuation application filed under 35 U.S.C. 111(a) claiming benefit under 35 U.S.C. 120 and 365(c) of PCT International Application No. PCT/JP2012/056028 filed on Mar. 8, 2012, designating the U.S., the entire contents of the foregoing application are incorporated herein by reference.

FIELD

The embodiments discussed herein are directed to an apparatus and method for inspecting a mounting state of an electronic component.

BACKGROUND

In recent years, a circuit board forming an electronic circuit by being mounted with electronic components has been miniaturized, and densification of circuit boards has been progressed. Among electronic components to be mounted on a circuit board, densification of a large scaled integrated circuit (LSI) has been progressed. With such a progress of densification, a number of external connection terminals of the LSI has been increased. On the other hand, the LSI is required to be miniaturized and densified. Thus, a ball grid array (BGA) type LSI, which is capable of being miniaturized while having a large number of pins, is used in many cases.

The BGA type LSI generally includes many solder-ball terminals as external connection terminals arranged in matrix on a mounting surface. Such a BGA type LSI is mounted to a circuit board by joining solder ball terminals to connection pads of the circuit board.

After mounting the LSI to the circuit board, an inspection is made as to whether all of the solder-ball terminals are joined to the respective connection pads of the circuit board. Each of the solder-ball terminals is once melted and solidified during a mounting process, thereby, forming a solder-joining part. Each electrode of the LSI is joined to the corresponding connection pad of the circuit board via the solder-joining part. Thus, by visually checking a state of the solder-joining part after mounting, a determination can be made as to whether each electrode of the LSI is appropriately connected to the corresponding connection pad of the circuit board via the solder-joining part.

However, because many solder-ball terminals are provided on the mounting surface of the BGA type LSI as mentioned above, it may be difficult to visually check many solder-joining parts existing in a narrow space between the circuit board and the LSI after the BGA type LIS is mounted to the circuit board. Thus, there is suggested an optical inspection method of inspecting a connecting state of solder joining parts by using an intensity of light (an amount of light) being irradiated to the solder-joining parts after mounting and passed through a space between the solder-joining parts (for example, refer to Patent Documents 1 to 3).

The following patent documents disclose a background art.

Patent Document 1: Japanese Laid-Open Patent Application No. 2001-144147

Patent Document 2: Japanese Laid-Open Patent Application No. 2006-41167

Patent Document 3: Japanese Laid-Open Patent Application No. 2000-346622

In a case where an inspection is made by detecting an intensity of transmitted light, which is irradiated onto one side of a space, in which many solder-joining parts are densely arranged, and transmitted to an opposite side of the space, if the density of the solder-joining parts is high and intervals therebetween become small, it may be difficult to detect a change in the transmitted light because an intensity of the transmitted light becomes low. Additionally, if the light is irradiated in a direction of alignment of the solder-joining parts, some of the solder-joining parts located at positions shaded by one of the solder-joining parts do not affect the transmitted light, and, thus, an inspection of the solder-joining parts cannot be done.

As mentioned above, in the case where an inspection is made on the solder-joining parts after an electronic component, such as a BGA type LSI having many solder-ball terminals arranged close to each other, is mounted to a circuit board, it may be difficult to make a reliable inspection if the above-mentioned inspection method using an intensity of a transmitted light is used.

Thus, it is desirous to materialize an electronic component inspection method and apparatus, which can make a reliable inspection on joint parts of an electronic component.

SUMMARY

There is provided according to an aspect of the embodiments an electronic component inspection apparatus including: a light source arranged in a mounting area where at least one electronic component is mounted to a board; a light-receiving sensor arranged outside the mounting area to detect an intensity of a light received from the light source; and a computer executing a program to perform a process of determining a state of joining parts in the mounting area based on a result of comparison of the intensity of the light received by the light-receiving sensor with an intensity of distribution previously acquired.

There is provided according to another aspect of the embodiments an electronic component inspection method, including: irradiating a light from inside a mounting area between a board and at least one electronic component mounted on the board toward a periphery of the mounting area; receiving the light exiting from the mounting area on outside the electronic component and acquiring an intensity distribution of the light; and comparing the acquired intensity distribution with a previously acquired intensity distribution and determining a state of joining parts in the mounting area.

There is provided according to a further aspect of the embodiments an electronic component inspection apparatus including: a light source arranged in a mounting area where at least one electronic component is mounted to a board; a light-receiving sensor receiving a light exiting from the mounting area and detecting an intensity of the received light; and a computer executing a program to perform a process of determining a state of joining parts in said mounting area based on a result of comparison of an intensity distribution of the light received by the light-receiving sensor with a previously acquired intensity distribution, wherein the light-receiving sensor spectrally disperses the light irradiated from the light source into a light having a predetermined wavelength range and detects an intensity of the light having the predetermined wavelength range.

The object and advantages of the embodiments will be realized and attained by means of the elements and combinations particularly pointed out in the appended claims.

It is to be understood that both the foregoing general description and the following detailed description are exemplary explanatory only and are not restrictive of the invention, as claimed.

BRIEF DESCRIPTION OF DRAWINGS

FIG. 8B is an illustration for explaining that a difference in incident angle of light affects a light incident on each cell of the line image sensor;

FIG. 9 is an illustration illustrating a structure in which three kinds of filters R, G and B are provided to each cell of the line image sensor;

FIG. 10 is a perspective view of a rotatable table;

FIG. 11A is an illustration illustrating a process of acquiring an intensity distribution while rotating the circuit board;

FIG. 12 is an illustration illustrating a process of mounting an LED to the circuit board;

FIG. 13 is an illustration illustrating a process of mounting an LED by embedding the LED into the circuit board;

DESCRIPTION OF EMBODIMENT(S)

A description will now be given, with reference to the drawings, of embodiments.

Figure 1:
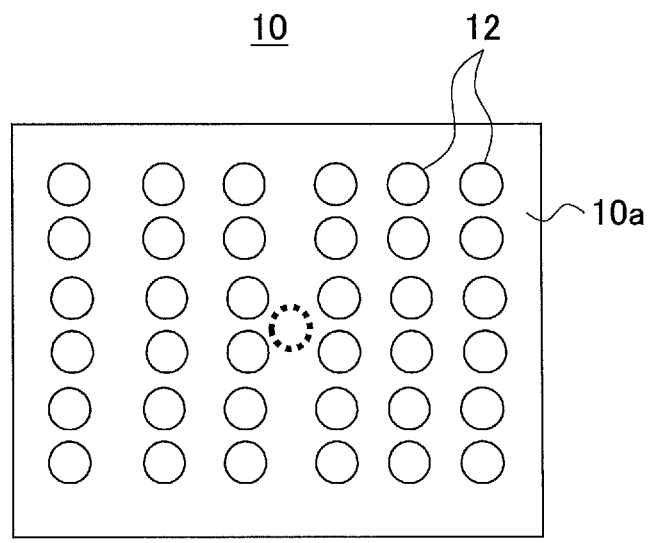
FIG. 1 is a plan view of a BGA type LSI.

First, a description is given of a first embodiment. In the first embodiment, a BGA type LSI is used as an example of an electronic component having many external connection terminals. FIG. 1 is a plan view of the BGA type LSI 10. The BGA type LSI 10 has a square external form. Many solder-ball terminals 12 serving as external connection terminals arranged in a matrix form are provided to a mounting surface 10a of the BGA type LSI 10 illustrated in FIG. 1.

Figure 2:
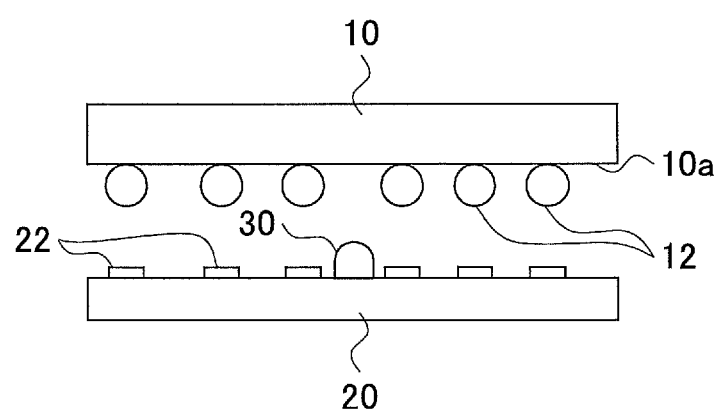
FIG. 2 is a side view of the BGA type LIS and a circuit board before mounting the BGA type LSI to the circuit board.

FIG. 2 is a side view of the BGA type LSI 10 and a circuit board 20 before mounting the BGA type LSI 10 to the circuit board 20. The circuit board 20 is, for example, a printed circuit board. By mounting various electronic components and electric components including a BGA type LSI 10 to the circuit board 20, An electronic circuit having a certain function is formed on the circuit board 20. Hereinafter, the BGA type LSI 10 may be simply referred to an LSI 10.

The present embodiment relates to an inspection apparatus and an inspection method for determining whether solder connection parts are good or bad by optically inspecting a mounting state after mounting the LSI 10 to the circuit board 20. The solder connection parts are formed by the solder-ball terminals 12 being once melted and solidified in a mounting process.

Figure 3:
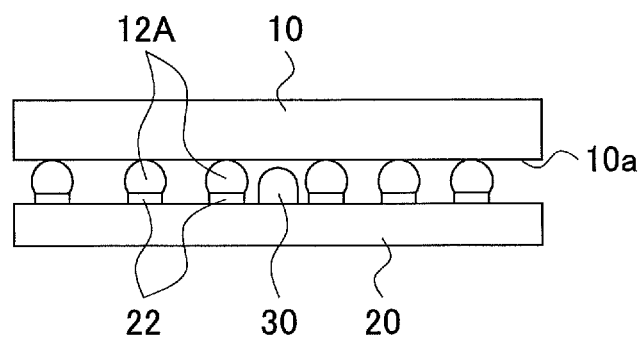
FIG. 3 is a side view of the BGA type LIS and the circuit board after mounting the BGA type LSI to the circuit board.

The mounting of the LSI 10 to the circuit board 20 is performed by placing the LSI 10 on the circuit board 20 while aligning a plurality of the solder-ball terminals 12 of the LSI 10 to respective connection pads 22 of the circuit board 20 and melting the solder-ball terminals 12 by reflowing and then solidifying the melted solder-ball terminals 12. FIG. 3 is a side view of the LSI 10 and the circuit board 20 after the LSI 10 is mounted to the circuit board 20. Electrodes (not illustrated in the figure) of the LSI 10 are mechanically connected to the connection pads 22 of the circuit board 20 by solder-joining parts 12A formed by the solder-ball terminals 12 being once melted and solidified again.

It should be noted that the "solder" is an example of a thermally meltable joining material as a joining material for joining the electrodes of the LSI 10 to the connection pads 22 of the circuit board 20. For example, a brazing material may be used as a thermally meltable joining material. Additionally, a joining material such as, for example, a conductive resin may be used as a joining material for joining the electrodes of the LSI 10 to the connection pads 22 of the circuit board 20.

The solder joining parts 12A exist between the mounting surface 10a of the LSI 10 and the circuit board 20 in an aligned state the same as the solder-ball terminals 12. In the present embodiment, as illustrated in FIGS. 2 and 3, a light emitting diode 30 (hereinafter, referred to as an LED 30) is provided on the circuit board 20 as a light source for irradiating light to the solder joining parts 12A. The LED 30 is located in a central part of an area on the circuit board 20 where the connection pads 22 are arranged in a matrix form. Accordingly, after the LSI 10 is mounted to the circuit board 20, the LED 30 is located at a center of a plurality of the solder joining parts 12A arranged in a matrix form, resulting in a state where the solder joining parts 12A are arranged around the LED 30.

Figure 4:
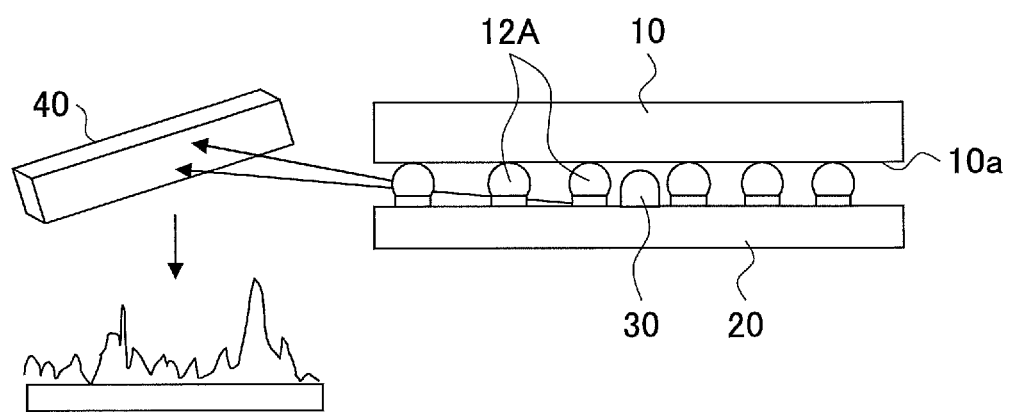
FIG. 4 is an illustration for explaining a structure of detecting an intensity distribution of light transmitted through between solder-joining parts by a line image sensor having a length corresponding to a side of the BGA type LSI.

The LED 30 is caused to emit light in a state where the LED 30 is located at the center of the area where a plurality of the solder joining parts 12A are arranged as mentioned above, and an intensity of the light that has passed through the spaces between the solder joining parts 12A is detected by an optical sensor provided outside the LSI 10. Thereby, an intensity distribution of the light over a predetermined length (range) corresponding to a length of the optical sensor is acquired. The predetermined length is set to, for example, a length corresponding to the one side of the LSI 10. That is, as illustrated in FIG. 4, a line image sensor 40 having a length corresponding to the one side of the LSI 10 is located on a side of one side of the LSI 10, and an intensity distribution of the light of the LED 30 that has passed through the spaces between the solder joining parts 12A is detected. Then, the detected intensity distribution of light is compared with an intensity distribution of light which is acquired using the LSI 10, which has been mounted to the circuit board 20 in a normal condition. If the two intensity distributions are substantially the same, a determination is made that the LSI 10 is mounted in a normal condition. It should be noted that, in FIG. 4, the pattern illustrated below the line image sensor 40 represents the intensity distribution of light detected by the line image sensor 40.

On the other hand, if the two intensity distributions are not equal and there is a difference between the two intensity distributions, it is determined that the mounted state of the LSI 10 that is being inspected is defective. For example, if an amount of solder of one of the solder-ball terminals 12 of the LSI 10 that is being inspected is too small, the solder joining part 12A becomes very small and differs from a normal shape, which results in an incomplete joining. Alternatively, if there is a portion where the solder-ball terminal 12 is not provided, a portion where the solder joining part 12A is not formed is created. Additionally, if the melted solder-ball terminals 12 are moved during a reflow process when mounting the LSI 10 to the circuit board 20, there may happen a case where the solder joining parts 12A are moved to different positions or a case where the adjacent solder joining parts 12A are integrated into one piece. Because either of these cases causes a defective mounting of the LSI 10, it is necessary perform an inspection to check whether these defects are present.

Figure 5:
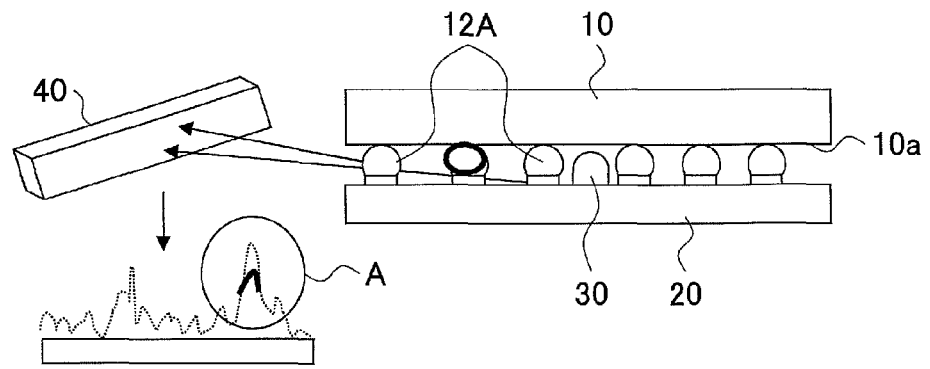
FIG. 5 is an illustration for explaining a method of determining whether a joint part is defective using a change in an intensity distribution.

Thus, as mentioned above, the light emitted from the LED 30 located at the center of the matrix arrangement of the solder joining parts 12A is detected outside the LSI 10. For example, if there is no solder joining part 12A at a position where the solder joining part 12A must exist in a normal condition, the light passing through the defective portion is affected. (That is, the light passes through the defective portion where the light cannot pass through in a normal condition where there is the solder joining part 12A formed at the position of the defective portion. That is, an intensity of the light received by the line image sensor 40 is affected by the defective portion. Thus, if there is the defective portion of the solder joining part 12A, a portion of the intensity distribution of the light received by the line image sensor 40 is changed from the intensity distribution of light obtained from the LSI 10, which is normally mounted (refer to a portion A indicated by a circle). The pattern indicated by dotted line in FIG. 5 represents the intensity distribution of light at a normal condition the same as the pattern indicated in FIG. 4. If there is a defective portion in one of the solder joining parts 12A, for example, a portion of the line indicating the intensity distribution is changed into a part indicated by a bold solid line in the portion A in FIG. 5, which results in a pattern different from the pattern obtained at the normal condition. Accordingly, if there is a portion different from a corresponding portion of the pattern indicating the intensity distribution of the light obtained from the normally mounted LSI 10 in the intensity distribution of the light received by the line image sensor 40, it can be determined that there is a defective portion among the solder joining parts 12A. The comparison of the intensity distributions can be performed using a pattern matching technique.

As mentioned above, the inspection can be made whether there is a detective portion in the solder joining parts 12A by irradiating light from the center of the area where a plurality of the solder joining parts 12A are two-dimensionally arranged and detecting an intention distribution of the light at outside of the mounting area (that is, the outside the LSI). In the present description, a portion or area where a plurality of the solder joining parts 12A are two-dimensionally arranged is defined as "mounting area". For example, in a case of an LSI having many terminals densely arranged, if light is irradiated from one side of the mounting area and to receive the light on the opposite side of the mounting area, the light may not transmit to the opposite side because a most part of the light is intercepted by the densely arranged solder joining parts 12A. However, according to the present embodiment, because the LED 30 is located at the center of the mounting area as a light source, a distance from the light source to the line image sensor 40 can be less than or equal to a half of a distance from a light source on one side of the mounting area to an image sensor on the opposite side of the mounting area. Thereby, according to the present embodiment, an intensity distribution of light can be surely obtained and a reliable inspection can be done.

There may be various arrangements and configurations of the above-mentioned line image sensor 40, which will be described later.

Here, according to the method of irradiating light from the outside of the mounting area in the direction of arrangement of the solder joining parts 12A and observing the light that has passed through the spaces between the solder joining parts 12A, some of the solder joining parts 12A located in a blind portion of one of the solder joining parts 12A cannot be an object to be inspected. The inspection including the measurement of an intensity of the transmitted light uses a change in the amount of light of the transmitted light, that is, whether the light is intercepted or transmitted through. Accordingly, if at least one of the solder joining parts 12A exists in a direction of travel of the light, there is no change in the amount of the transmitted light irrespective of whether there are other solder joining parts 12A behind (blind portion) the one of the solder joining parts 12A. Thus, is difficult to inspect whether the solder joining parts 12A exist normally in the blind portion.

Thus, according to the present embodiment, an accuracy of detection of a defective portion can be improved by using a diffraction light diffracted by the solder joining parts 12A as the light detected by the line image sensor 40. However, the light passed through a space extremely close to the solder joining part 12A is changed in its direction of travel due to diffraction of light. An angle of light changed by diffraction depends on a wavelength of the light. Thus, a state of the solder joining parts 12A can be more reliably inspected by measuring a spectral distribution of the wavelength of the diffracted light, which can go round to the blind portion of the solder joining part 12A, rather than merely observing an intensity distribution obtained by detecting a transmitted light.

Figure 6:
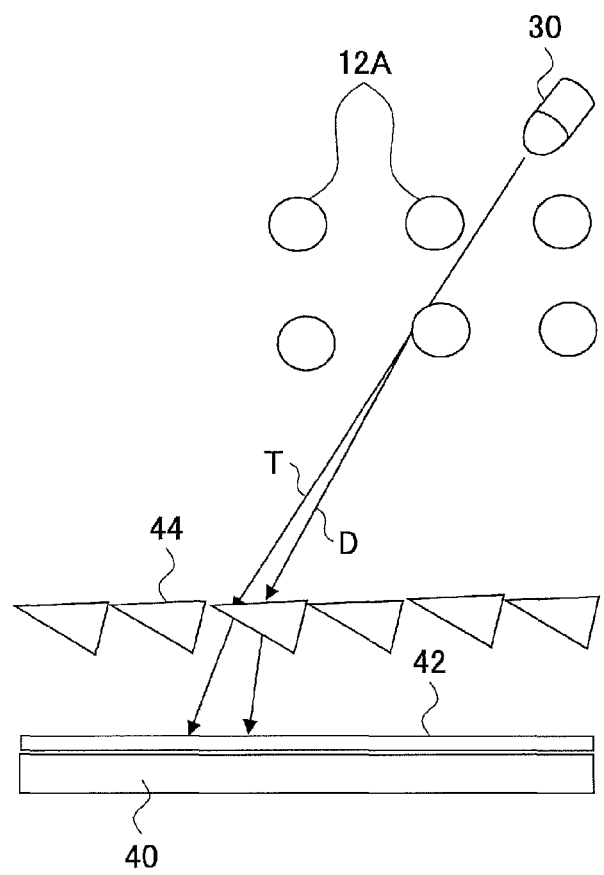
FIG. 6 is an illustration illustrating an outline structure of a spectral distribution observation of wavelength of diffraction light.

A description is given of an example of the structure for observing a spectral distribution of a wavelength of a diffracted light. FIG. 6 is an illustration illustrating an outline structure of observing a spectral distribution of a wavelength of a diffracted light. In the example of FIG. 6, a color filter 42 is arranged in front of the line image sensor 40, and further a micro-prism array 44 is arranged in front of the color filter 42.

The light emitted by the LED 30 (it is assumed that the LED 30 is a white light LED) is incident on the micro-prism array 44 after transmitting through the spaces between the solder joining parts 12A as indicated by an arrow T in FIG. 6. At this time, the light passed through a portion extremely close to the solder joining part 12A is changed in its direction of travel due to diffraction of light as indicated by an arrow D and, then, the light travelling in the direction of the arrow D is incident on the color filter 42. The color filter 42 is, for example, a combination of filters each of which transmits only a predetermined monochromatic light (light of a predetermined wavelength area).

Figure 7:
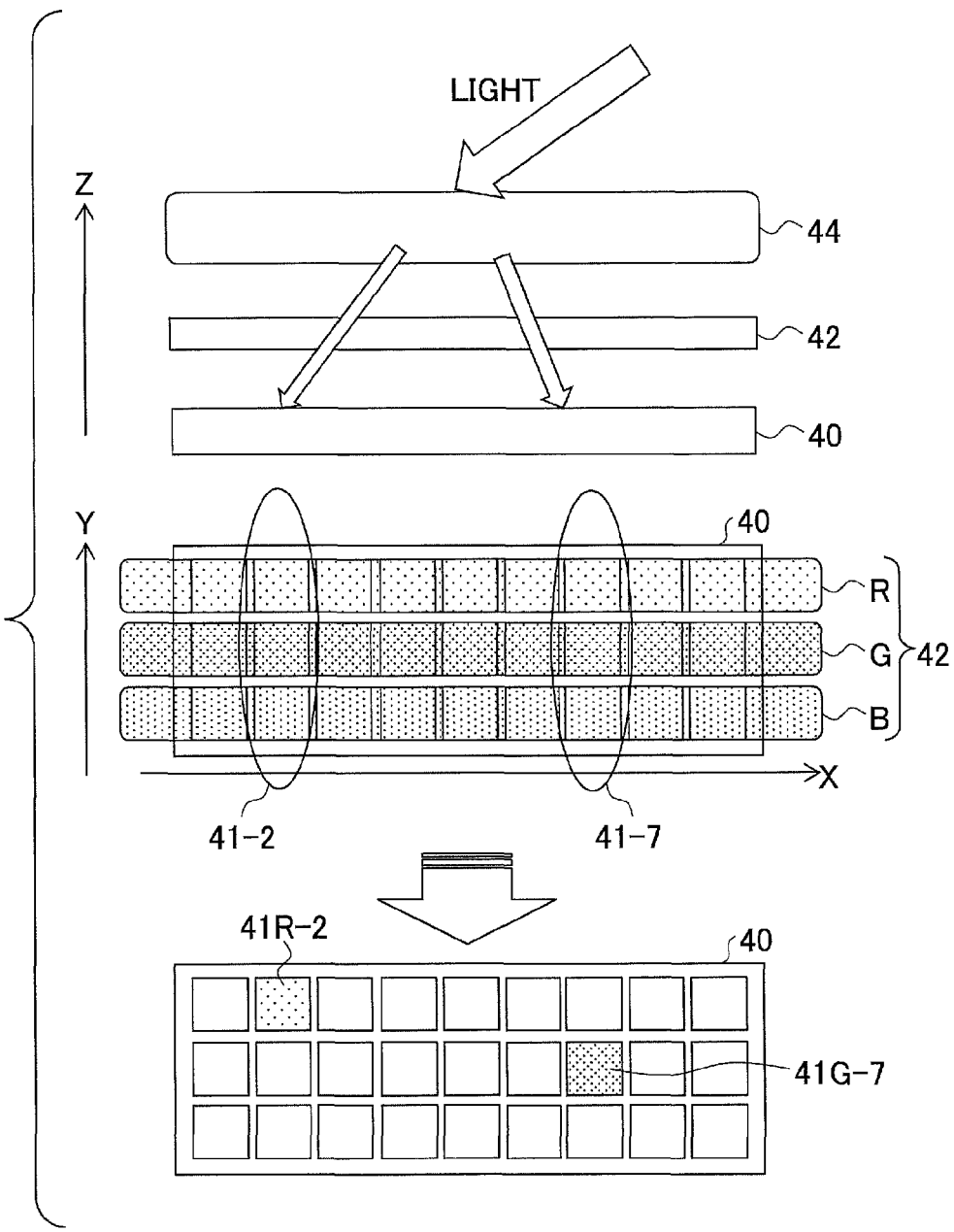
FIG. 7 is an illustration for explaining a function of a color filter and a micro-prism array illustrated in FIG. 6.

FIG. 7 is an illustration for explaining functions of the color filter 42 and the micro-prism array 44. The micro-prism array 44 is formed by two-dimensionally arranging many small prisms to as to be a prism formed in a flat shape as a whole. The color filter 42 is a combination of filters each of which selectively transmits a respective one of a plurality of monochromatic lights. For example, as illustrated in FIG. 7, the color filter 42 is formed by combining a filter R which transmits only a light of a wavelength corresponding to red, a filter G which transmits only a light of a wavelength corresponding to green and a filter B which transmits only a light of a wavelength corresponding to blue. The line image sensor arranged beneath the color filter is divided into many cell groups 41-$n$ ($n$ is an integer) that are aligned in a longitudinal direction of the line image sensor. Each of the cell groups 41-$n$ includes three cells 41R-n, 41G-n and 41B-n that are aligned in a transverse direction of the line image sensor 40. Each of the cells 41R-n, 41G-n and 41B-n detects a light incident thereon.

In the above-mentioned structure, a white light incident on the micro-prism array 44 at a certain angle is spectrally dispersed by a spectral action of the micro-prism array 44. The spectrally dispersed light is incident on the color filter 42, and only a light having a wavelength corresponding to red is transmitted through the filter R. Similarly, only a light having a wavelength corresponding to green is transmitted through the filter G, and only a light having a wavelength corresponding to blue is transmitted through the filter B. Accordingly, the light incident on each cell of the line image sensor 40 is a light having only one of the wavelengths corresponding to read, green and blue.

In the example illustrated in FIG. 7, only a red light spectrally dispersed is incident on the cell group 41-2, and only a green light wavelength spectrally dispersed light is incident on the cell group 41-7. Accordingly, the cell group 41-2 can detect an intensity (an amount) of only red light from among the spectrally dispersed lights. Similarly, the cell group 41-2 can detect an intensity (an amount) of only green light from among the spectrally dispersed lights.

Figure 8A:
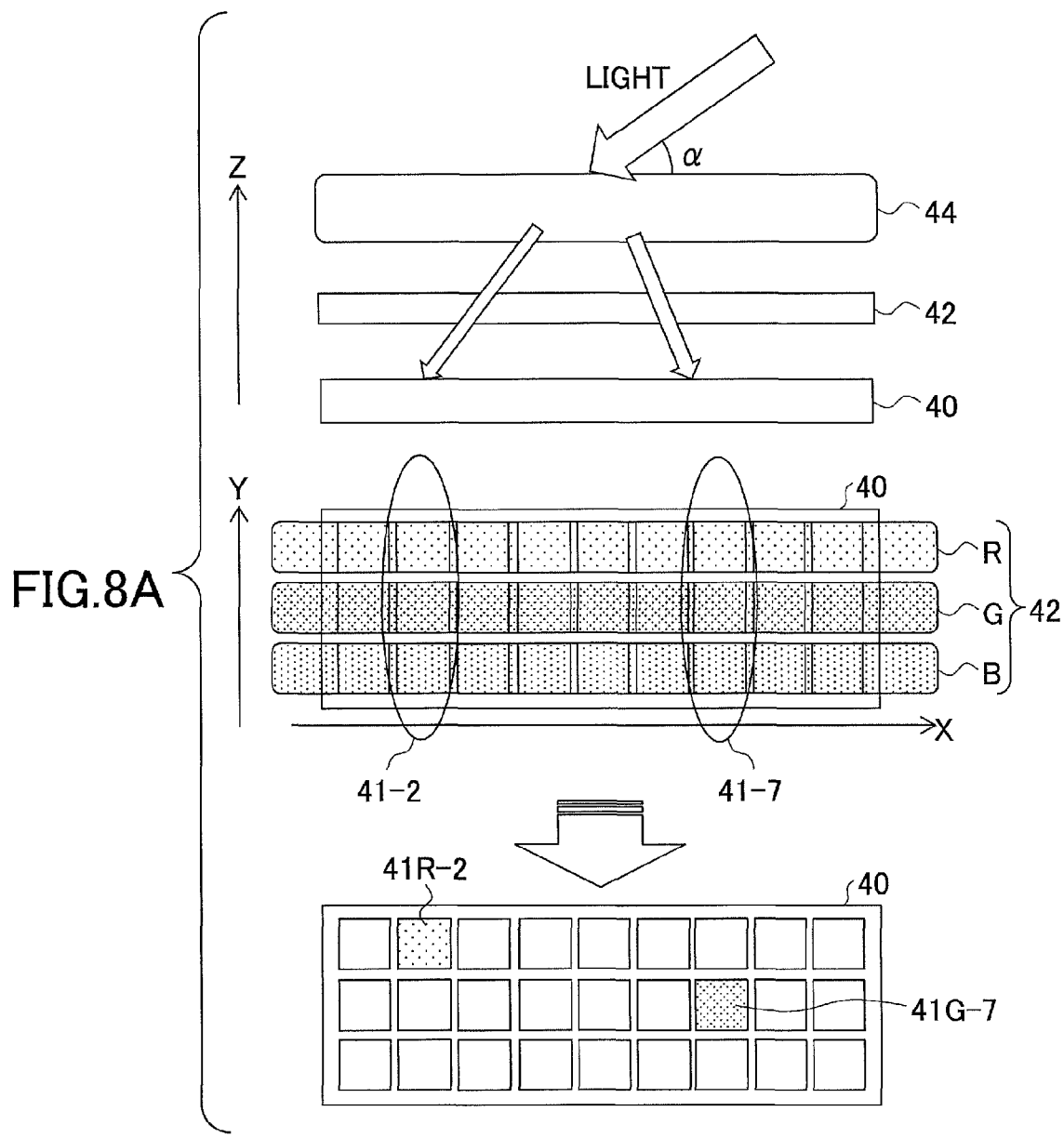
FIG. 8A is an illustration for explaining that a difference in incident angle of light affects a light incident on each cell of the line image sensor.

The color (wavelength) of the light incident on each cell group 41-$n$ is determined by an incident angle of the white light incident on the micro-prism array 44 after diffracted by the solder joining parts 12A. FIGS. 8A and 8B are illustrations for explaining how a difference in incident angle affects the light incident on each cell group 41-$n$.

In FIG. 8A, the incident angle of the light incident on the micro-prism array 44 is $\alpha$. In FIG. 8B, the incident angle of the light incident on the micro-prism array 44 is $\beta$, which is larger than the incident angle $\alpha$. With the incident angle $\alpha$ of FIG. 8A, the red light from among the lights output after spectrally dispersed by the micro-prism array 44 is incident on the cell 41R-2, and the green light from among the lights output after spectrally dispersed by the micro-prism array 44 is incident on the cell 41G-7. On the other hand, with the incident angle $\beta$ of FIG. 8B, the red light from among the lights output after spectrally dispersed by the micro-prism array 44 is incident on the cell 41R-3, and the green light from among the lights output after spectrally dispersed by the micro-prism array 44 is incident on the cell 41G-8.

As mentioned above, an amount of light detected at each position (by each cell) of the line image sensor 40 changes according to an incident angle of the light incident on the micro prism-array 44. The light incident on the micro-prism array 44 contains a diffracted light, which is the light emitted from the LED and diffracted by the solder joining parts 12A, which changes a direction of travel of the light. Thus, according to the combination of the micro-prism array 44, the color filter 42 and the line image sensor 40 as illustrated in FIG. 7, a spectral distribution characteristic of the diffracted light can be obtained.

After the intensities of the lights of the three colors (R, G, B) are acquired, a synthesized intensity distribution is acquired by synthesizing these lights. Then, a tristimulus value or a chromaticity coordinate that represents a characteristic of the synthesized intensity distribution is acquired by calculation, and is compared with one that has been acquired from a normal one.

As mentioned above, because the diffracted light generated at one of the solder joining parts 12A goes round to the backside of the one of the solder joining parts 12, the diffracted light passes through the backside of the one of the solder joining parts 12A. That is, viewed from the LED 30 (light source), the diffracted light travels to a blind portion behind the one of the solder joining parts 12A. Thus, the diffracted light is irradiated onto other solder joining parts 12A located in the blind portion behind the one of the solder joining parts 12A. Accordingly, a change in the shape of one of the solder joining parts 12A, which exists in a blind portion behind one of the solder joining parts 12A, or nonexistence of one of the solder joining parts 12A, which exists in a blind portion behind one of the solder joining parts 12A, appears as a change in the spectral distribution characteristic of the diffracted light. Thus, the spectral distribution characteristic of the diffracted light is compared with the spectral distribution characteristic previously obtained from the LSI 10, which is normally mounted, in order to reliably determine a state of the solder joining parts 12A.

In the above-mentioned structure, three kinds of spectral distribution characteristics are acquired individually by the color filter 42, which is three-color filters (R, G, B), and the intensity distribution at wavelength corresponding to each color is observed. However, these spectral distribution characteristics may be synthesized into one intensity distribution and compares to the intensity distribution with the normal. Additionally, as illustrated in FIG. 9, the three color filters R, G, B may be provided to each of the cells of the line image sensor 40 so that each of the cells detects the light of one of the three colors.

The reason for obtaining the intensity distribution from the lights of a plurality of colors (wavelengths) is because an amount of diffraction is changed according to wavelength. By observing the lights of a plurality of wavelengths and observing the light having a wavelength of which a change in the intensity distribution is largest, an accuracy of determination can be improved.

It should be noted that the color filter 42 is not always provided to the line image sensor 40. For example, in a case where a light source emitting a monochromatic light is used as the light source, the color filter is not needed. Additionally, when a sufficient spectral dispersion is obtained by diffraction at the solder joining parts 12A or when a high-accuracy is not required for determination, the color filter 42 may not be provided.

Additionally, the LED 30 as a light source is not limited to a white light emitting diode, and may be a monochromatic light LED, or LEDs of different colors (for example, three kinds of R, G, B) may be combined as a single light source. Additionally, when a monochromatic light LED is used, it is desirous to use an LED having a wide color-generating wavelength range.

The LED 30 can irradiate light toward all of the solder joining parts 12A by arranging the single LED 30 at the center of the mounting area if the LED 30 is an omnidirectional LED, which can emit light toward all of the solder joining parts 12A. However, without using such an omnidirectional LED, a plurality of directional LEDs, each of which can emit only in directions within a specific range, may be combined to cover an entire circumference. Alternatively, a directional LED may be caused to rotate 360 degrees to irradiate light in all directions.

Next, a description is given in detail of a position of the LED 30 as a light source and a configuration and arrangement of the line image sensor 40 as a light-receiving sensor.

The LED 30 is provided inside the mounting area, which is an area where many solder joining parts 12A are formed, in a state where the LSI 10 is mounted to the circuit board 20. Then, the line image sensor 40 is outside the mounting area, that is, outside the LSI 10. It is desirous to provide the LED 30 at substantially center of the mounting area as mentioned above, but the location of the LED 30 is not limited to the center of the mounting area. If the LED 30 is located inside the mounting area, the single LED 30 can emit light in directions toward all solder joining parts 12A in the mounting area, and the light (including the transmitted light and the diffracted light) exiting out of the mounting area can be received by the line image sensor 40, which is located outside the mounting area.

For example, if there is a portion (the solder joining parts 12A) for which a state of joint is to be checked, the LED 30 may be arranged further inside the mounting area than the portion to be checked and in the vicinity of the portion to be checked. Thereby, a distance from the light source to the solder joining parts 12A to be checked and a distance from the light source to the light-receiving sensor can be reduced, which permits a reliable inspection on the solder joining parts 12A at arbitrary positions.

In the present embodiment, a description is given on the assumption that the LED as a light source is located inside the mounting area and at the center of the mounting area. By locating the light source at the center of the mounting area, if the line image sensor 40 as a light-receiving sensor is located outside the mounting area and along one side of the LSI, a distance from the light source to the light-receiving sensor can be reduced to be smaller than or equal to a half of the distance of the case where the mounting area is located between the light source and the light-receiving sensor. Thereby, even where a number of solder joining parts 12A in the mounting area is large and a density of the solder joining parts 12A is high, the light from the light source is surely reaches to the light-receiving sensor, which permits a reliable inspection.

If the LED 30 is located at the center of the mounting area, the single line image sensor 40 can be arranged along one side of the LSI 10. In this case, in order to perform an inspection on all of the solder joining parts 12A in the mounting area, as illustrated in FIG. 10, a rotating mechanism 52 is provided to a table 50, which is a placement stage for placing the circuit board 20 after mounting the LSI 10. The table 50 on which the circuit board 20 is placed so that one side of the LSI 10 opposes to the line image sensor 40 is rotated, and an intensity distribution of the light exiting from the one side of the LSI 10 is acquired by the line image sensor 40. Thereafter, the table 50 is rotated by driving the rotating mechanism 52 by a predetermined angle (may be 90 degrees), and an intensity distribution of the light exiting from another side of the LSI is acquired by the line image sensor 40 at a position where the another side of the LSI 10 faces the line image sensor 40. This operation is repeated to acquire intensity distributions of the lights exiting from all four sides of the LSI 10 so as to inspect all of the solder joining parts 12A between the LSI 10 and the circuit board 20.

Figure 11B:
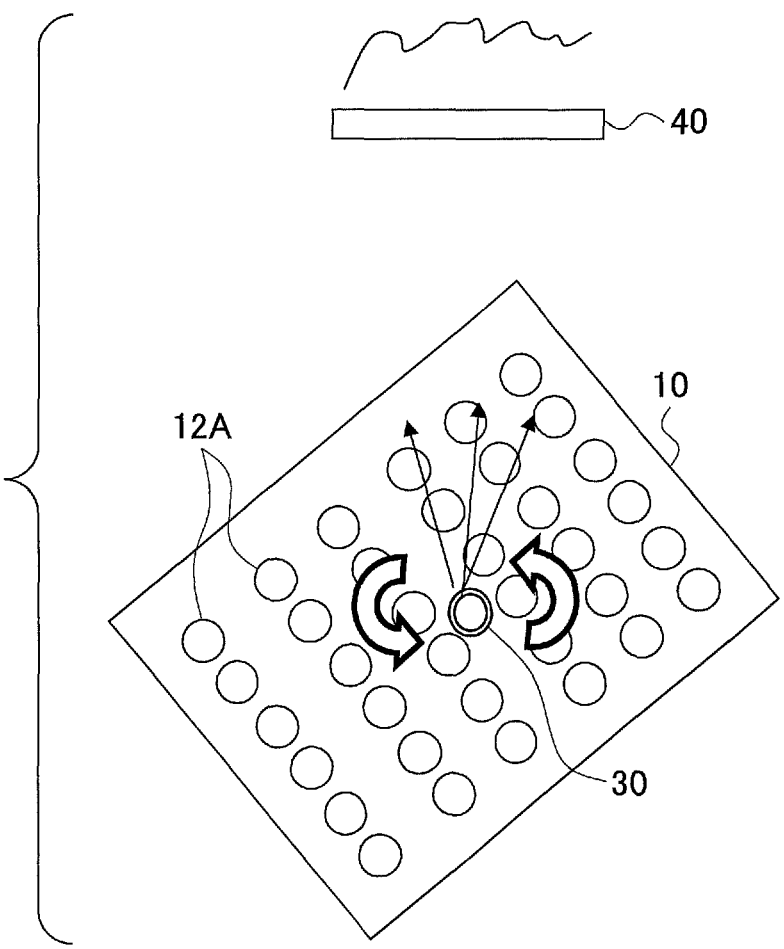
FIG. 11B is an illustration illustrating a process of acquiring an intensity distribution while rotating the circuit board.
Figure 11C:
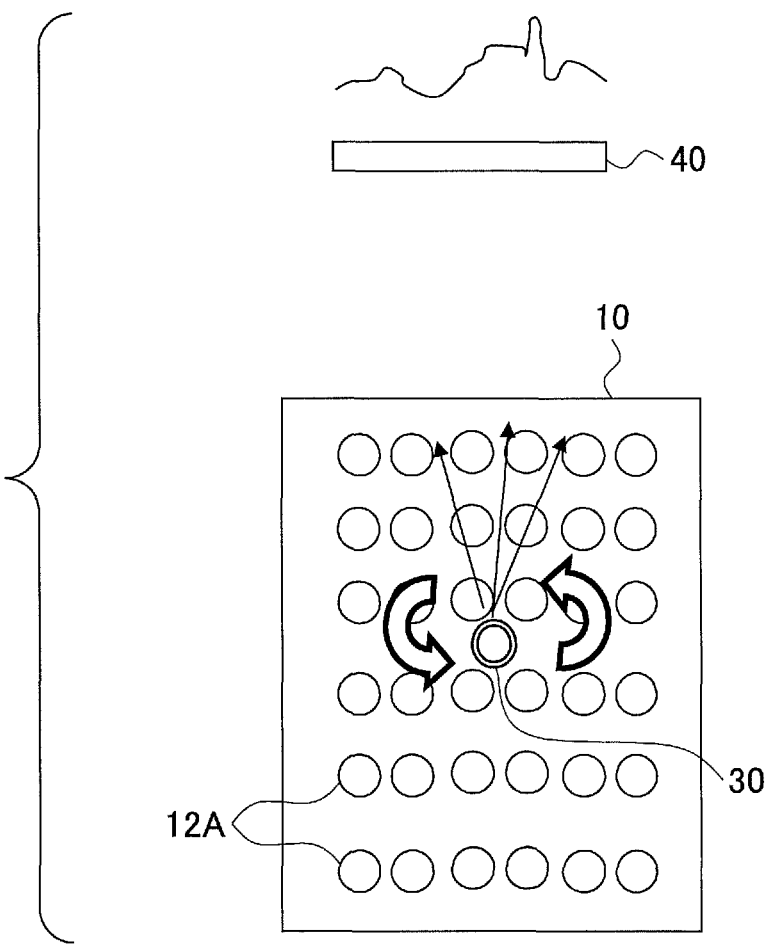
FIG. 11C is an illustration illustrating a process of acquiring an intensity distribution while rotating the circuit board.

Additionally, when using the table 50 rotatable by the rotating mechanism 52, the line image sensor 40 may be made shorter than a length of one side of the LSI 10 so as to acquire an intensity distribution by continuously receiving the light by the line image sensor 40 while rotating the LSI 10 and the circuit board 20. That is, an intensity distribution is acquired by the line image sensor 40 in the state illustrated in FIG. 11A, and, then, an intensity distribution is acquired by the line image sensor 40 in a state where the LSI 10 is rotated to a position illustrated in FIG. 11B, and, thereafter, an intensity distribution is acquired by the line image sensor 40 in a state where the LSI 10 is rotated to a position illustrated in FIG. 11C. This measuring operation is continued until the LSI 10 makes a full turn, and, thereafter, an intensity distribution for the entire circumference (four sides of the LSI 10) is acquired by connecting the acquired intensity distributions, and the thus-acquired intensity distribution is compared with a previously acquired intensity distribution in a normal condition. It should be noted that, in FIGS. 11A, 11B and 11C, the pattern illustrated above the line image sensor 40 is a pattern representing the intensity distribution detected by the line image sensor 40.

A description is given below of a method of mounting the LED 30 as a light source to the circuit board 20. FIG. 12 is an illustration illustrating a process of mounting the LED 30 to the circuit board 20. First, the circuit board 20 is prepared (refer to FIG. 12-(a)), and, then, electrodes 24A and 24B for connecting LED are formed by copper plating on an LED mounting part of the circuit board 20 (refer to FIG. 12-(b)). Consequently, nickel-plating or gold-plating is applied onto the electrodes 24A and 24B for connecting LED, and, then, a solder paste is applied onto the plated electrodes 24A and 24B (refer to FIG. 12-(c)). Then, the LED 30 is mounted on the electrodes 24A and 24B via the solder paste (refer to FIG. 12-(d)). Thereafter, the LED 30 is soldered to the electrodes 24A and 24B for connecting LED by reflowing the solder paste (refer to FIG. 12-(e)).

FIG. 13 is an illustration for explaining a process of mounting the LED 30 by embedding the LED 30 into the circuit board 20. First, the circuit board 20 is prepared (refer to FIG. 13-(a)), and, then, an embedding hole 26 is formed in an LED mounting part of the circuit board 20 (refer to FIG. 13-(b)). Consequently, electrodes 24A and 24B for connecting LED are formed on an inner surface of the embedding hole 26 by copper-plating (refer to FIG. 13-(c)). Consequently, nickel-plating or gold-plating is applied onto the surfaces of the electrodes 24A and 24B for connecting LED (refer to FIG. 13-(d)). Then, the LED 30 is embedded into the embedding hole 26 and electrodes of the LED 30 is joined to the electrodes 24A and 24B for connecting LED (refer to FIG. 13-(e)).

Although the LED as a light source is mounted to the circuit board 20 in the above-mentioned embodiments, the light source is not always mounted to the circuit board 20. That is, when the LSI 10 is mounted to the circuit board 20, the light source is located inside the mounting area where the solder joining parts 12A are arranged between the LSI 10 and the circuit board 20. Specifically, for example, a light source (for example, the LED 30) is inserted from the backside of the circuit board 20 and is caused to protrude into the mounting area between the LSI 10 and the circuit board 20. Alternatively, The LED 30 as a light source may be mounted on the mounting surface 10a of the LSI 10.

Figure 14:
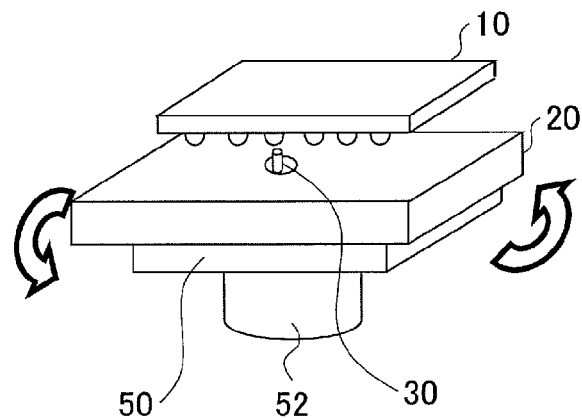
FIG. 14 is a perspective view illustrating a structure in which an LED is inserted into a circuit board from a backside.
Figure 15:
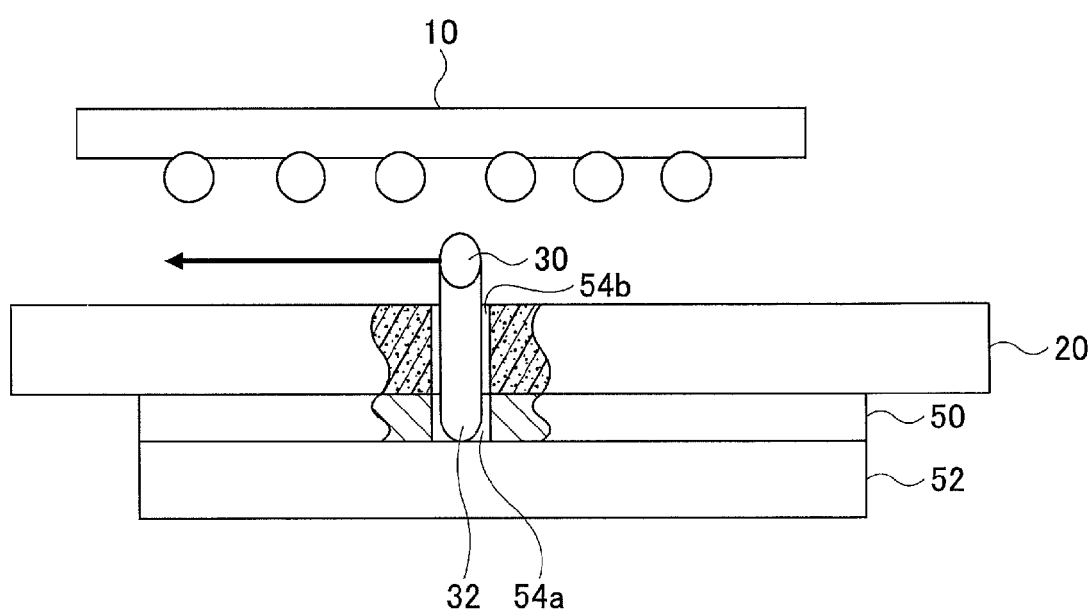
FIG. 15 is a side view illustrating a structure in which an LED is inserted into a circuit board from a backside.

A description is given below of an example of inserting a light source (for example, the LED 30) into the circuit board 20 from a backside of the circuit board 20. FIG. 14 is a perspective view illustrating a structure of inserting the LED 30 into the circuit board 20 from a backside of the circuit board 20. FIG. 15 is a side view illustrating a structure of inserting the LED 30 into the circuit board 20 from a backside of the circuit board 20. Although the LSI 10 is illustrated as if it is apart from the LSI in FIG. 15 for the sake of convenience of illustration, the LSI 10 is actually mounted to the circuit board 20 and the solder joining parts 12A are formed in the mounting area.

The LED 30 is attached to an end of an elongated support member 32. The support member 32 extends from underneath the table 50, penetrates through a through hole 54a, and protrudes from the placement surface of the table 50. Accordingly, the LED 30 attached to an end of the support member 32 protrudes from the placement surface of the table 50. The circuit board 20 mounted with the LSI 10 is placed on the table 50 so that the protruding LED 30 is inserted into the through hole 54b of the circuit board 20. Thereby, the LED 30 penetrates through the through hole 54b of the circuit board 20 and is set in a state where the LED 30 is located in the mounting area between the LSI 10 and the circuit board 20.

The through hole 54a of the table 50 is formed at the center of rotation. The support member 32 for supporting the LED 30 inserted into the through hole 54a is located at the center of the rotation and does not rotate even when the table is rotated. Additionally, the line image sensor 40 located outside the LSI 10 is also fixed at a fixed position. Accordingly, when the table 50 is rotated, portions of the LSI 10 and the circuit board which portions are located between the LED 30 and the line image sensor 40 rotationally move relatively to the LED 30. In this case, a directivity of the light emitting direction is given to the LED 30 so that a light may be emitted always to a direction toward the line image sensor 40. Because the circuit board 20 mounted with the LSI 10 is rotated by rotating the table 50, all of the solder joining parts 12A in the mounting area can be subjected to an inspection.

It should be noted that although the LED 30 is attached to the elongated support member 32 to serve as a light source in the above-mentioned example, other light-emitting devices may be used instead of the LED 30. Alternatively, the support member 32 may be formed by an optical fiber so that lights are irradiated from an end of the optical fiber to a periphery.

Figure 16:
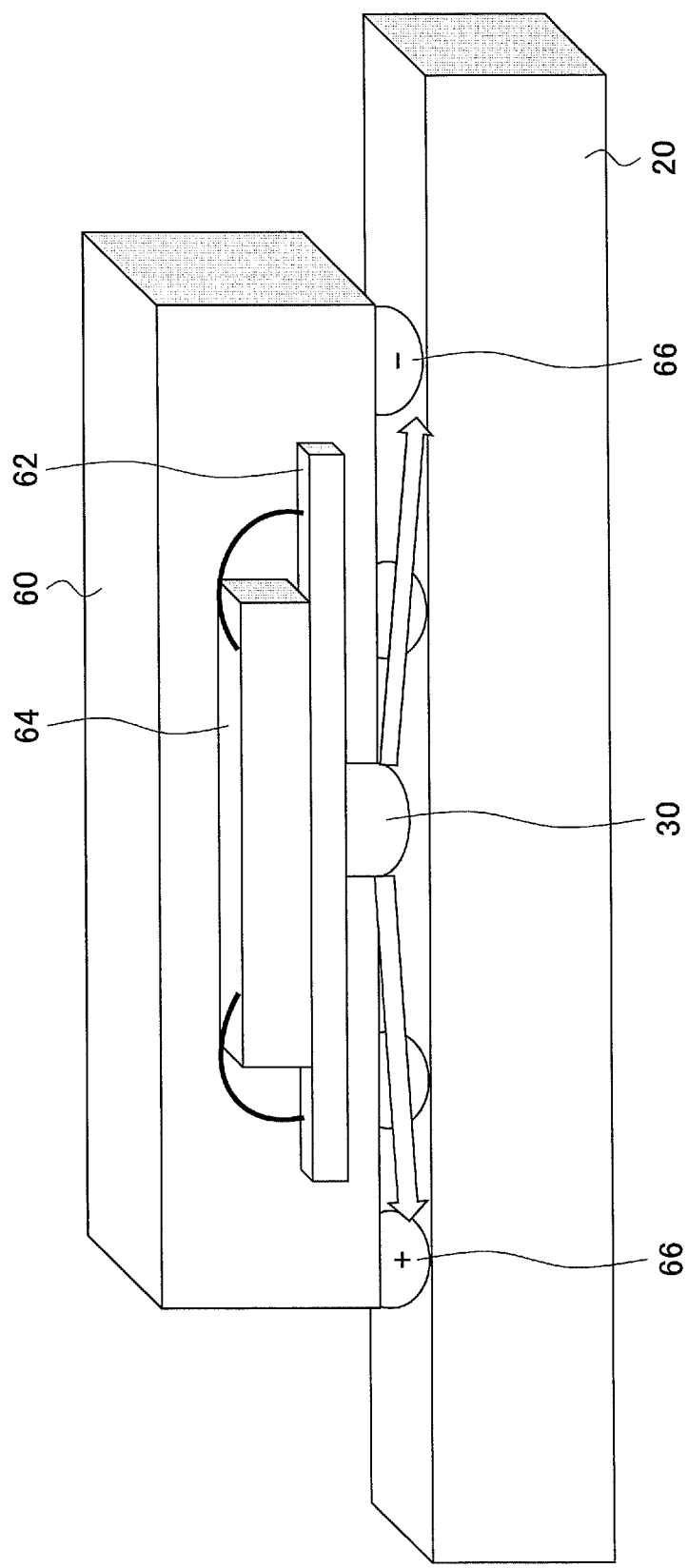
FIG. 16 is a perspective view of an interior of an LSI having an LED embedded therein.

Next, a description will be given of an example of providing a light source to an LSI. FIG. 16 is a perspective view illustrating an interior of an LSI in which the LED 30 is embedded. The LED 30 is embedded in the LSI 60 illustrated in FIG. 16. The LED 30 is mounted to a backside of a board 62 inside the package of the LSI 60. A semiconductor chip 64 is mounted on a surface of the board 62, and the LED 30 is mounted on a side opposite to the semiconductor chip 64.

The LED 30 is encapsulated so that a top portion of the LED 30 is exposed from the package. The LSI 60 is a BGA type LSI, which has a plurality of solder-ball terminals 66. Two of the solder-ball terminals 66 are connected to electrodes of the LED 30 to activate the LED 30. For example, two outermost solder-ball terminals 66 among the plurality of solder-ball terminals 66 are connected to a positive (+) terminal and a negative (−) terminal of the LED 30, respectively. The two outermost solder-ball terminals 66 are terminals for activating LED and formed in solder joining parts after the LSI 60 is mounted to the circuit board 20. When activating the LED 30, an electric current is supplied from the circuit board 20 to the LED 30 through the two solder-ball terminals 66. The terminals for activating LED may be provided on a top surface or a side surface of the LSI 60.

Figure 17:
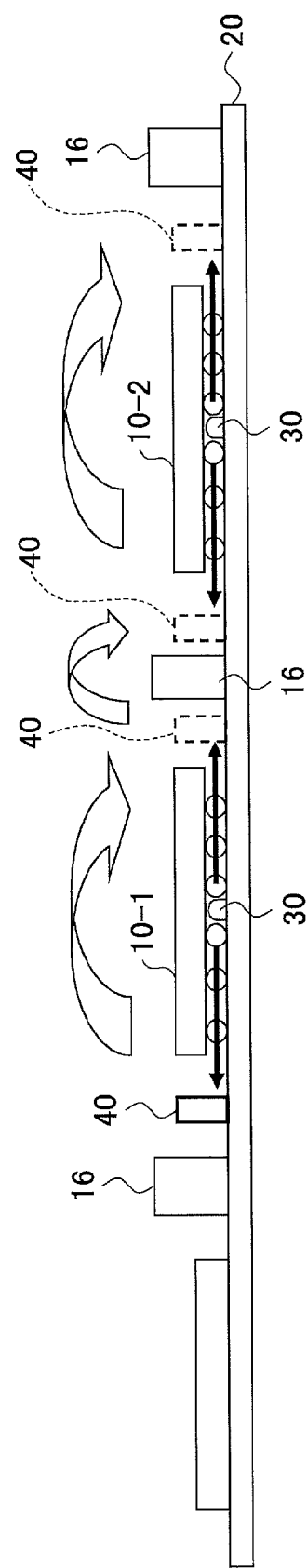
FIG. 17 is an illustration for explaining a process of inspecting an LSI on a circuit board.

Next, a description is given of an example of arrangement of the line image sensor 40 as a light-receiving sensor. Generally, the circuit board 20 to which the LSI 10 is mounted is much larger than the LSI 10. As illustrated in FIG. 17, a plurality of LSIs may be mounted to the circuit board 20 or other electronic components may be mounted to the circuit board 20 in many cases. In order to inspect the mounted state of the circuit board 20 mounted with a plurality of LSIs, the LED 30 is located at the center of the mounting area of each of the LSIs and intensity distributions are acquired while sequentially moving the line image sensor 40 above the circuit board 20.

Referring to FIG. 17, the line image sensor 40 is arranged along one side of the LSI 10-1 mounted on the circuit board 20 while avoiding a contact with other electronic components 16, and a light irradiated from the LED 30 is received by the line image sensor 40 to acquire an intensity distribution. After ending the acquisition of the intensity distribution, the line image sensor 40 is moved to a position along another side of the LSI 10-1 while avoiding a contact with other electronic components 16 to acquire an intensity distribution. After the acquisition of intensity distributions for the four sides of the LSI 10-1, the line image sensor 40 is moved to a position along one side of another LSI 10-2 to acquire an intensity distribution. As mentioned above, an inspection for a plurality of LSIs can be performed by sequentially moving the single line image sensor 40.

Figure 18:
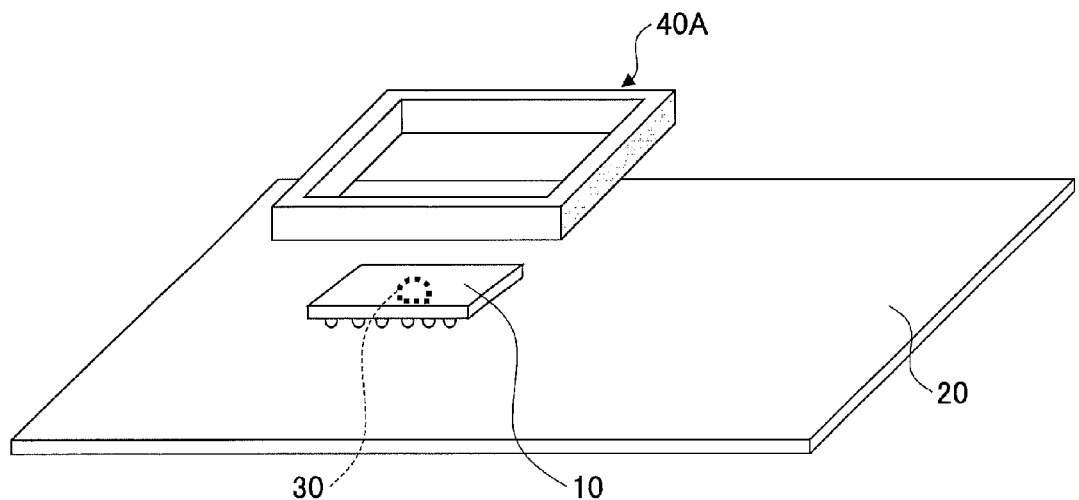
FIG. 18 is a perspective view of a line image sensor formed to surround an entire LSI.

However, if there is no electronic component around the LSI 10, a line image sensor 40A having a frame shape may be used to entirely surround the LSI 10 as illustrated in FIG. 18. The lights exiting from four sides of the LSI are received by the line image sensor 40A to acquire intensity distributions. In this case, the LED 30 may be an omnidirectional LED, which can irradiate lights toward all radial directions. In this case, measurements for the four sides of the LSI 10 can be performed at once simultaneously. If, for example, the LED 30 is arranged outside the mounting area (outside the LSI 10), measurements can be made for at most three sides of the LSI 10. In order to perform measurements for all four sides, a measurement for some sides may be made and, thereafter, the line image sensor 40 must be moved to a position at which measurements can be made for other sides for which the measurements have not been made. Accordingly, when the LED 30 is located at the center of the mounting area and measurements are performed at once for all of the four sides of the LSI 10, a time spent on an inspection can be reduced.

Figure 19:
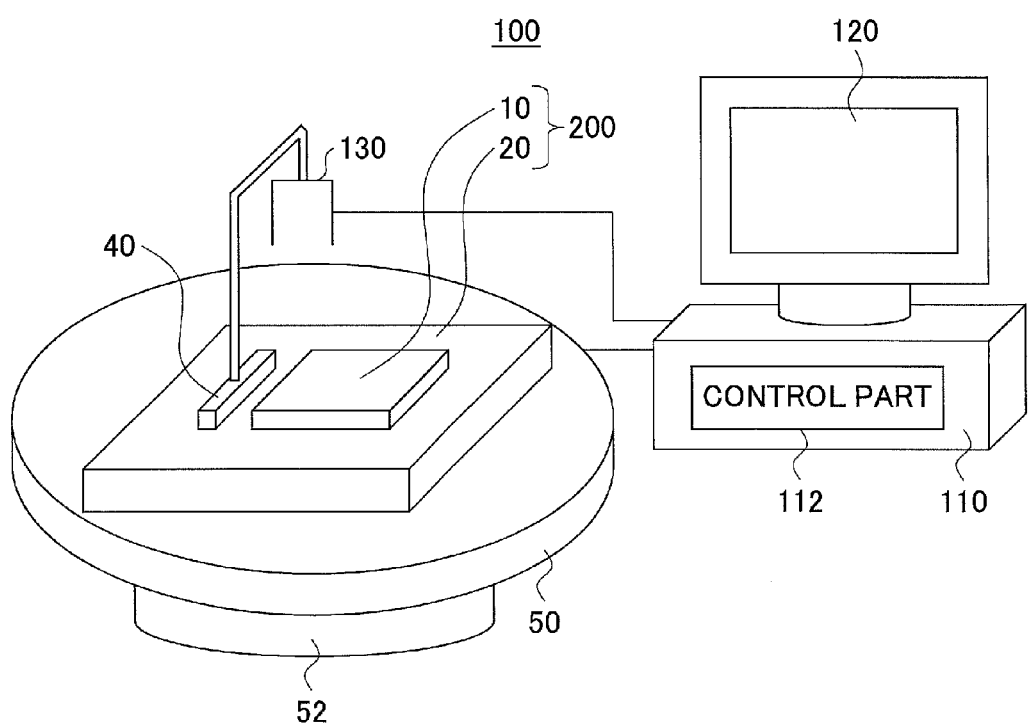
FIG. 19 is an illustration illustrating an entire structure of an inspection apparatus.

Next, a description is given, with reference to FIG. 19, of an entire structure of an inspection apparatus according to the present embodiment.

The inspection apparatus 100 includes a table 50, a light-receiving sensor (for example, the line image sensor 40), an inspection apparatus main unit 110 and an inspection result display device 120. An object to be inspected 200 (for example, the circuit board 20 mounted with the LSI 10) is placed on the table 50. The object to be inspected 200 includes a plurality of solder joining parts 12A to be inspected and a light source (for example, the LED 30) located inside the mounting area.

The line image sensor 40 is located at a position along one side of the object to be processed 200 placed on the table 50. The line image sensor 40 is moved by a moving device 130 controlled by the inspection apparatus main unit 110. The moving device 130 causes the line image sensor 40 to move upward and downward and leftward and rightward and also rotate in either direction. The moving device 130 is controlled and driven by the inspection apparatus main unit 110. The inspection apparatus main unit 110 includes a control part 112, which includes a processing unit such as a microcomputer or the like. The inspection apparatus main unit 110 causes a rotating mechanism 52 and the moving device 130 to drive to move the line image sensor 40 to a desired inspection position relative to the object to be inspected 200.

The control part 120 of the inspection apparatus main unit 110 processes an intensity of light received by the line image sensor 40 to acquire an intensity distribution. Then, the control part 112 compares the acquired intensity distribution with a normal intensity distribution, which is previously acquired in a normal condition and saved in a memory, so as to determine a quality (whether good or bad) of the solder joining parts. The inspection apparatus main unit 110 sends a result of the determination to the inspection result display device 120 to display the result of the determination on the inspection result display device 120.

The inspection process performed by the inspection apparatus 100 is as follows. First, the line image sensor 40 is placed at a desired position relative to the object to be processed 200 placed on the table 50. Then, the LED 30 located in the mounting area is activated to emit a light, and the light emitted from the LED 30 is received by the line image sensor 40. Intensity information regarding an intensity of the light detected by the line image sensor 40 is sent to the inspection apparatus main body 110.

The control part 112 of the inspection apparatus main unit 112 compares the acquired intensity distribution or spectral analysis result information with a normal intensity distribution or normal spectral analysis result information previously stored in the memory so as to determine whether the object to be processed 200 is good or bad.

It should be noted that it can be determine the quality (whether good or bad) based on only the acquired intensity distribution or the spectral analysis result without using the previously acquired normal intensity distribution or spectral analysis result. Considering, for Example, the object to be processed 200 located at a position where the solder joining parts 12A are located at a position pint-symmetric to the LED 30. If intensity distributions are acquired for the four sides of the object to be processed 200 mentioned above and if the acquired intensity distributions are substantially the same with each other, the object to be processed 200 can be determined as a good object because a probability of having an abnormality is low. In other words, if there is at least one of the four intensity distributions differs from other intensity distributions, the object to be process 200 is determined as a defective object because that difference is due to an abnormality in one of the solder joining parts 12A.

All examples and conditional language recited herein are intended for pedagogical purposes to aid the reader in understanding the principles of the invention and the concepts contributed by the inventor to furthering the art, and are to be construed a being without limitation to such specifically recited examples and conditions, nor does the organization of such examples in the specification relates to a showing of the superiority and inferiority of the invention. Although the embodiment(s) of the present invention (s) has (have) been described in detail, it should be understood that the various changes, substitutions, and alterations could be made hereto without departing from the spirit and scope of the invention.

What is claimed is:

1. An electronic component inspection apparatus comprising:
   a light source disposed in a mounting area where at least one electronic component is mounted on a board;
   a light-receiving sensor disposed outside the mounting area and configured to receive a spectrally dispersed light having a wavelength in a predetermined wavelength range after a light emitted by the light source passes through spaces between joining parts in the mounting area, and detect an intensity of the spectrally dispersed light; and
   a computer configured to
      acquire an intensity distribution of the spectrally dispersed light by performing spectral analysis on the intensity of the spectrally dispersed light detected by the light-receiving sensor,
      compare the acquired intensity distribution with a previously acquired intensity distribution, and
      determine a state of the joining parts based on a result of the comparison.

2. The electronic component inspection apparatus as claimed in claim 1, further comprising:
   a placement table on which the board with the electronic component mounted on the board is placed; and
   a rotating mechanism to rotate the placement table.

3. The electronic component inspection apparatus as claimed in claim 1, wherein the light-receiving sensor includes a line image sensor having a length corresponding to one side of the electronic component.

4. The electronic component inspection apparatus as claimed in claim 1, wherein the light-receiving sensor includes a line image sensor having a frame form to surround an entire periphery of the electronic component.

5. The electronic component inspection apparatus as claimed in claim 1, wherein the light source is provided to an end of a support member inserted into a through hole penetrating the board.

6. The electronic component inspection apparatus as claimed in claim 1, wherein the light source includes a white light emitting diode, and the light-receiving sensor includes a color filter that selectively transmits a light of a predetermined color.

7. The electronic component inspection apparatus as claimed in claim 1, wherein the light source is a monochromatic light emitting diode.

8. An electronic component inspection method, comprising:
   emitting a light from a light source disposed in a mounting area between a board and at least one electronic component mounted on the board toward a periphery of the mounting area;

receiving, by a light-receiving sensor disposed outside the mounting area, a spectrally dispersed light having a wavelength in a predetermined wavelength range after the light emitted by the light source passes through spaces between joining parts in the mounting area, to detect an intensity of the spectrally dispersed light;

acquiring, by a computer, an intensity distribution of the spectrally dispersed light by performing spectral analysis on the intensity of the spectrally dispersed light detected by the light-receiving sensor;

comparing the acquired intensity distribution with a previously acquired intensity distribution; and determining a state of the joining parts based on a result of the comparison.

9. The electronic component inspection method as claimed in claim 8, further comprising:

providing a placement table on which the board with the electronic component mounted on the board is placed, and a rotating mechanism to rotate the placement table; and rotating, by the rotating mechanism, the electronic component together with the placement table before the spectrally dispersed light is received by the light-receiving sensor.

* * * * *